(12) United States Patent
Gonzalez et al.

(10) Patent No.: US 11,039,879 B2
(45) Date of Patent: Jun. 22, 2021

(54) ABLATION DEVICE

(71) Applicant: Spiration, Inc., Redmond, WA (US)

(72) Inventors: Hugo X. Gonzalez, Woodinville, WA (US); Christine N. Jurevicius, Issaquah, WA (US); Brandon J. Shuman, Redmond, WA (US); Zoie R. Engman, Kirkland, WA (US); Cassandra R. Saleira, Redmond, WA (US)

(73) Assignee: GYRUS ACMI, INC., Westborough, MA (US)

( * ) Notice: Subject to any disclaimer, the term of this patent is extended or adjusted under 35 U.S.C. 154(b) by 642 days.

(21) Appl. No.: 15/761,599

(22) PCT Filed: Oct. 4, 2016

(86) PCT No.: PCT/US2016/055338
§ 371 (c)(1),
(2) Date: Mar. 20, 2018

(87) PCT Pub. No.: WO2017/069940
PCT Pub. Date: Apr. 27, 2017

(65) Prior Publication Data
US 2018/0344389 A1    Dec. 6, 2018

Related U.S. Application Data

(60) Provisional application No. 62/307,291, filed on Mar. 11, 2016, provisional application No. 62/243,961, filed on Oct. 20, 2015.

(51) Int. Cl.
*A61B 18/12* (2006.01)
*A61B 18/14* (2006.01)
(Continued)

(52) U.S. Cl.
CPC .......... *A61B 18/1477* (2013.01); *A61B 8/481* (2013.01); *A61B 2017/00867* (2013.01);
(Continued)

(58) Field of Classification Search
CPC ...... A61B 18/1477; A61B 2018/00065; A61B 2018/00083; A61B 2018/00196;
(Continued)

(56) References Cited

U.S. PATENT DOCUMENTS 4,869,259 A    9/1989  Elkins et al.
5,318,564 A *  6/1994  Eggers ............... A61B 18/1233
                                                        606/47
(Continued)

FOREIGN PATENT DOCUMENTS

CN    102225024 A    10/2011
EP       2626030 A2    8/2013
(Continued)

OTHER PUBLICATIONS

U.S. Appl. No. 14/662,975, filed Mar. 19, 2015, by Brandon J. Shuman et al. All pages U.S. Appl. No. 14/638,655, filed Mar. 4, 2015, by Brandon J. Shuman et al. All pages.

*Primary Examiner* — Daniel W Fowler
(74) *Attorney, Agent, or Firm* — Clements Bernard Walker; Michael S. Smith

(57) ABSTRACT

An electrosurgical device includes a needle with an interior surface defining a lumen and a first electrode positioned within the lumen of the needle in a first position. The first electrode is movable within the needle between the first position and a plurality of other positions. The first electrode extends beyond a distal end of the needle in the plurality of other positions and includes one or more anchors that pierce into a predetermined portion of tissue in an anatomy of a (Continued)

patient. The first electrode is energized to ablate the predetermined portion of tissue with the first electrode.

14 Claims, 5 Drawing Sheets

(51) Int. Cl.
*A61B 8/08* (2006.01)
*A61B 18/00* (2006.01)
*A61B 18/16* (2006.01)
*A61B 90/00* (2016.01)
*A61B 17/00* (2006.01)

(52) U.S. Cl.
CPC .............. *A61B 2018/00065* (2013.01); *A61B 2018/00083* (2013.01); *A61B 2018/00196* (2013.01); *A61B 2018/00214* (2013.01); *A61B 2018/00279* (2013.01); *A61B 2018/00577* (2013.01); *A61B 2018/00589* (2013.01); *A61B 2018/00994* (2013.01); *A61B 2018/143* (2013.01); *A61B 2018/1432* (2013.01); *A61B 2018/1475* (2013.01); *A61B 2018/162* (2013.01); *A61B 2090/034* (2016.02); *A61B 2090/062* (2016.02); *A61B 2090/0811* (2016.02)

(58) Field of Classification Search
CPC ........... A61B 2018/00214; A61B 2018/00279; A61B 2018/00577; A61B 2018/00589; A61B 2018/00994; A61B 2018/143; A61B 2018/1432; A61B 2018/1475; A61B 2018/162
See application file for complete search history.

(56) References Cited

U.S. PATENT DOCUMENTS

| | | | |
|---|---|---|---|
| 5,427,115 A | 6/1995 | Rowland et al. | |
| 5,507,743 A | 4/1996 | Edwards et al. | |
| 5,514,131 A * | 5/1996 | Edwards ............ | A61B 10/0233 128/898 |
| 5,672,173 A | 9/1997 | Gough et al. | |
| 5,846,241 A * | 12/1998 | Kittur ................ | A61B 18/1492 606/48 |
| 5,855,576 A | 1/1999 | Leveen et al. | |
| 5,951,547 A | 9/1999 | Gough et al. | |
| 5,980,517 A | 11/1999 | Gough et al. | |
| 6,050,992 A | 4/2000 | Nichols | |
| 6,090,105 A | 7/2000 | Zepeda et al. | |
| 6,306,132 B1 * | 10/2001 | Moorman .......... | A61B 10/0233 600/562 |
| 6,379,353 B1 | 4/2002 | Nichols | |
| 6,416,510 B1 | 7/2002 | Altman et al. | |
| 6,551,311 B2 | 4/2003 | Lee et al. | |
| 6,638,277 B2 | 10/2003 | Schaefer et al. | |
| 6,749,604 B1 | 6/2004 | Eggers et al. | |
| 6,929,637 B2 | 8/2005 | Gonzalez et al. | |
| 7,195,629 B2 | 3/2007 | Behl et al. | |
| 7,357,798 B2 | 4/2008 | Sharps et al. | |
| 7,419,488 B2 | 9/2008 | Ciarrocca et al. | |
| 7,434,578 B2 | 10/2008 | Dillard et al. | |
| 7,520,877 B2 | 4/2009 | Lee, Jr. et al. | |
| 7,524,318 B2 | 4/2009 | Young et al. | |
| 7,533,671 B2 | 5/2009 | Gonzalez et al. | |
| 7,691,151 B2 | 4/2010 | Kutsko et al. | |
| 7,842,061 B2 | 11/2010 | Dillard et al. | |
| 7,918,795 B2 | 4/2011 | Grossman | |
| 8,043,286 B2 | 10/2011 | Palanker et al. | |
| 8,073,551 B2 | 12/2011 | McCann et al. | |
| 8,114,071 B2 | 2/2012 | Woloszko et al. | |
| 8,187,270 B2 | 5/2012 | Auth et al. | |
| 8,361,066 B2 | 1/2013 | Long et al. | |
| 8,656,928 B2 | 2/2014 | Carlson et al. | |
| 2002/0042565 A1 | 4/2002 | Cooper et al. | |
| 2002/0059938 A1 * | 5/2002 | Fogarty .................. | A61B 90/39 128/899 |
| 2002/0147446 A1 * | 10/2002 | Ein-Gal ............. | A61B 18/1477 606/41 |
| 2003/0028231 A1 | 2/2003 | Partridge et al. | |
| 2003/0233099 A1 | 12/2003 | Danaek et al. | |
| 2004/0059328 A1 | 3/2004 | Daniel et al. | |
| 2004/0254572 A1 | 12/2004 | McIntyre et al. | |
| 2005/0139570 A1 | 6/2005 | Lambert et al. | |
| 2006/0078501 A1 | 4/2006 | Goertz et al. | |
| 2006/0142824 A1 * | 6/2006 | Zikorus ................ | A61B 18/082 607/96 |
| 2006/0206111 A1 | 9/2006 | Young | |
| 2007/0043350 A1 | 2/2007 | Soltesz et al. | |
| 2007/0123964 A1 * | 5/2007 | Davies ............... | A61B 18/1492 607/116 |
| 2008/0319436 A1 | 12/2008 | Daniel et al. | |
| 2009/0321458 A1 | 12/2009 | Blair et al. | |
| 2010/0004723 A1 | 1/2010 | Foster et al. | |
| 2010/0128608 A1 | 5/2010 | Zou et al. | |
| 2010/0324637 A1 | 12/2010 | Trip et al. | |
| 2011/0238057 A1 | 9/2011 | Moss et al. | |
| 2011/0295262 A1 | 12/2011 | Germain et al. | |
| 2012/0016364 A1 | 1/2012 | Mayse et al. | |
| 2012/0052485 A1 | 3/2012 | Shany et al. | |
| 2012/0059247 A1 | 3/2012 | Speeg et al. | |
| 2012/0059308 A1 | 3/2012 | Hsu et al. | |
| 2012/0101380 A1 | 4/2012 | Blum et al. | |
| 2012/0209116 A1 | 8/2012 | Hossack et al. | |
| 2012/0271163 A1 | 10/2012 | Foster et al. | |
| 2012/0316559 A1 | 12/2012 | Mayse et al. | |
| 2013/0085397 A1 | 4/2013 | Ramamurthy et al. | |
| 2013/0204068 A1 | 6/2013 | Gnanashanmugam et al. | |
| 2013/0190609 A1 | 7/2013 | Fischer, Jr. | |
| 2013/0226026 A1 | 8/2013 | Dillard et al. | |
| 2013/0289529 A1 | 10/2013 | Caira et al. | |
| 2013/0310823 A1 | 11/2013 | Gelfand et al. | |
| 2014/0008375 A1 | 1/2014 | Zanus et al. | |
| 2014/0018788 A1 | 1/2014 | Engelman et al. | |
| 2014/0039315 A1 | 2/2014 | Davies et al. | |
| 2014/0066917 A1 * | 3/2014 | Cosman, Jr. ........ | A61B 18/1477 606/33 |
| 2014/0076764 A1 | 3/2014 | Wang et al. | |
| 2014/0107642 A1 * | 4/2014 | Rios ................ | A61B 17/320016 606/41 |
| 2015/0005769 A1 | 1/2015 | Klink et al. | |
| 2015/0272542 A1 | 10/2015 | Shuman et al. | |
| 2015/0272662 A1 | 10/2015 | Shuman et al. | |
| 2016/0256216 A1 | 9/2016 | Chang et al. | |

FOREIGN PATENT DOCUMENTS

| | | |
|---|---|---|
| EP | 2662116 A1 | 11/2013 |
| JP | 2006334242 A | 12/2006 |
| JP | 2007519489 A | 7/2007 |
| JP | 2011125632 A | 6/2011 |
| JP | 2013502274 A | 1/2013 |
| WO | 9605123 A1 | 2/1996 |
| WO | 1999025260 A1 | 5/1999 |
| WO | 2011161474 A1 | 12/2011 |
| WO | 2012100355 A1 | 8/2012 |
| WO | 2013059511 A1 | 4/2013 |
| WO | 2013169927 A1 | 11/2013 |
| WO | 2013173481 A2 | 11/2013 |
| WO | 2015061621 A1 | 4/2015 |
| WO | 2015148077 A1 | 10/2015 |

* cited by examiner

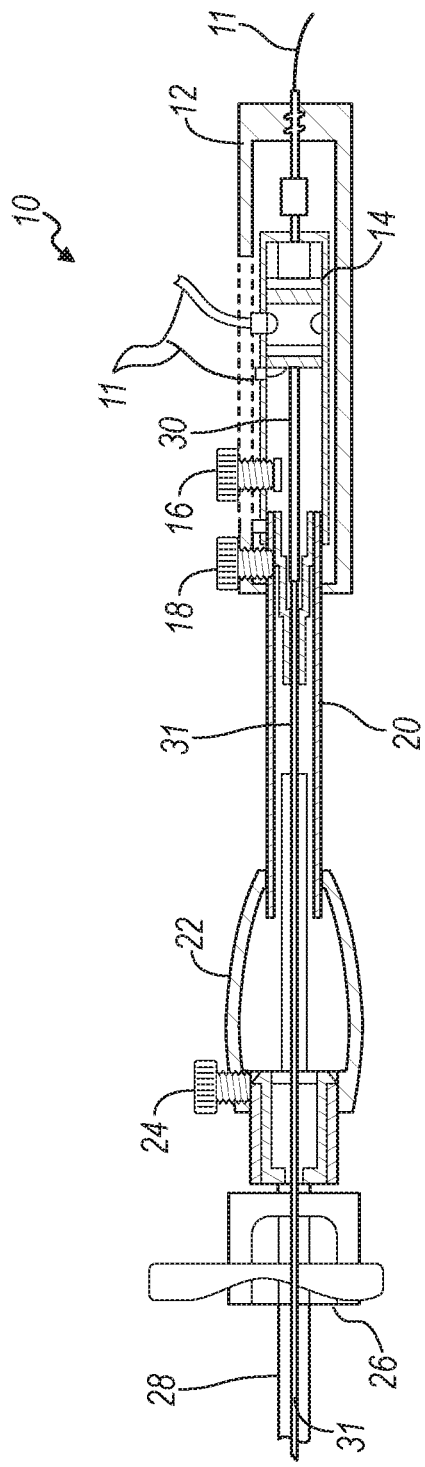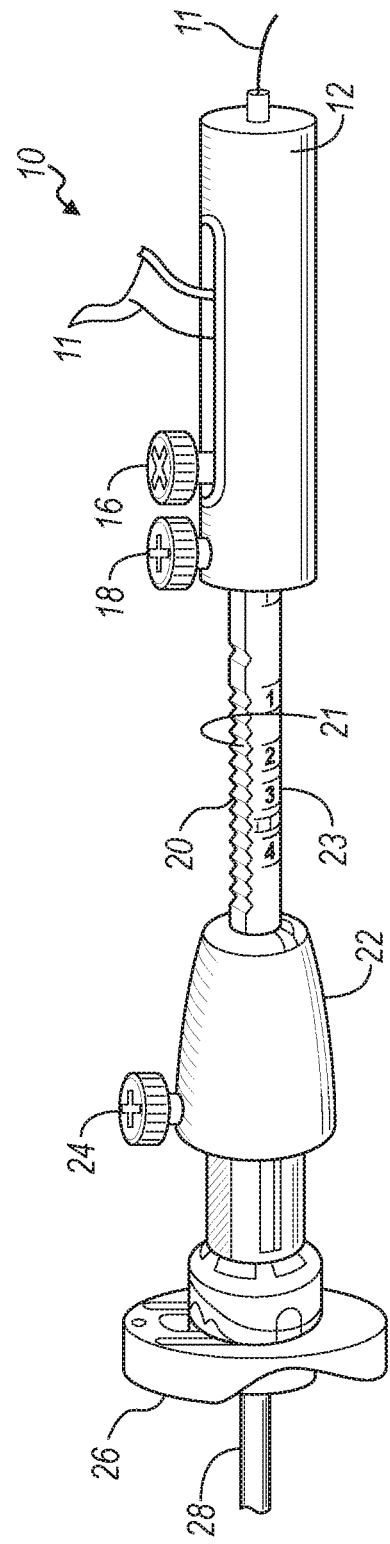
FIG. 1A
FIG. 1B

ABLATION DEVICE

RELATED APPLICATION

This application claims the benefit of U.S. Provisional Patent Application No. 62/243,961, filed on Oct. 20, 2015, and U.S. Provisional Patent Application No. 62/307,291, filed on Mar. 11, 2016.

The contents of above applications are incorporated herein by reference in their entirety.

FIELD

The present disclosure relates to an electrosurgical device. More specifically, the present disclosure relates to an ablation device with anchoring features.

BACKGROUND

The statements in this section merely provide background information related to the present disclosure and may or may not constitute prior art.

Lung nodules, lesions, tumors, and other cancerous or precancerous regions of tissue in the lung may be difficult to treat with invasive surgical techniques, with attendant complications such as excessive bleeding, infection risk, air leaks, pneumothorax, and other such issues. In particular, regions deep in the lung may be difficult to access using conventional methods, further increasing the difficulty of treatment.

It is contemplated that the device of the present invention may also be used to treat nodules, lesions, tumors, and other cancerous or precancerous regions of tissue in any other region of the body where an endoscope may be inserted, used for diagnostic purposes, or along with therapeutic instrumentation, including the gastrointestinal tract, sinus passages and the urinary system, for example.

The current methods for tissue coagulation involves either placing the electrode in a single location and coagulate or moving it to different locations in the target to coagulate in order to improve coagulation volume, improve the margin around the target, and produce a more spherical coagulation. However, the placement algorithm used in these tech geeks is ambiguous and may not solve issues with over-penetration affecting the coagulation volume or efficiency, nor does it specify a consistent method to reproduce the coagulation zone. The major issue with single location coagulation is that there is a diminishing effect of coagulation through the application of high-frequency electromagnetic energy when attempting to increase the coagulation volume. The coagulation volume is also highly susceptible to the shape and orientation of the electrode(s). These issues arise from the limitations occurring in the conductivity of the tissue decreases as it is coagulated and the electrical path increasing in length, resulting in greater impedance and significantly lower efficiency.

SUMMARY

The present invention provides an improved medical device with at least one electrode that is energized to ablate a predetermined portion of tissue in a patient.

Accordingly, pursuant to one aspect of the invention, there is contemplated a medical device that includes a needle with an interior surface defining a lumen and a first electrode positioned within the lumen of the needle in a first position. The first electrode is movable within the needle between the first position and a second position. The first electrode extends beyond a distal end of the needle in the second position and includes one or more anchors that pierce into a predetermined portion of tissue in an anatomy of a patient. The first electrode is energized to ablate the predetermined portion of tissue with the first electrode.

The medical device may be further characterized by one or any combination of the features described herein, such as, for example: the needle serves as a second electrode, the first electrode and the needle arranged to deliver a desired level of energy to the predetermined portion of tissue when the first electrode is in the second position to ablate the predetermined portion of tissue; the medical device further includes an insulator that electrically isolates the needle from the first electrode; the needle has echogenic features on the exterior of the needle; the echogenic features are a plurality of circular slots spaced apart along a portion of the exterior of the needle; the first electrode is attached to a wire that extends through the lumen of the needle; the wire is made of a shape memory alloy; the shape memory alloy is nitinol; the first electrode is attached to the wire with a tube crimped to the first electrode and the wire; the tube includes echogenic features; the echogenic features are a plurality of dents distributed about the exterior of the tube; and at least one of the one or more anchors includes a tip that pierces into the predetermined portion of tissue and a curved member that latches onto the predetermined portion of tissue to secure the first electrode to the predetermined portion of tissue.

In another aspect, the present disclosure provides a method of treating a predetermined portion of tissue in a patient's anatomy including one or more of the following steps: positioning a first electrode within a lumen of a needle; positioning a distal end of the needle at the predetermined portion of tissue; retracting the needle relative to the first electrode so that the first electrode extends beyond the distal end of the needle, the first electrode including one or more anchors that pierce into the predetermined portion of tissue; and energizing the first electrode to ablate the predetermined portion of tissue with the first electrode.

The method may be further characterized by one or any combination of the features described herein, such as, for example: the needle serves as a second electrode, the first electrode and the needle arranged to deliver a desired level of energy to the predetermined portion of tissue when the first electrode is in the second position to ablate the predetermined portion of tissue; and at least one of the one or more anchors includes a tip that pierces into the predetermined portion of tissue and a curved member that latches onto the predetermined portion of tissue to secure the first electrode to the predetermined portion of tissue.

A method of coagulation used during coagulation. The technique utilizes the needle track created during penetration into the target to coagulate along the needle path, starting at the deepest location first, then procedurally coagulating at locations along the needle path that are closer to the initial penetration location. This method creates a more consistent and reproducible coagulation volume, while reducing the limitations of high tissue impedance.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings:

FIG. 1A is a side cross-sectional view of an electrosurgical device in accordance with the principles of the present invention;

FIG. 1B is an exterior view of the electrosurgical device shown in FIG. 1A;

DETAILED DESCRIPTION

Figure 2:
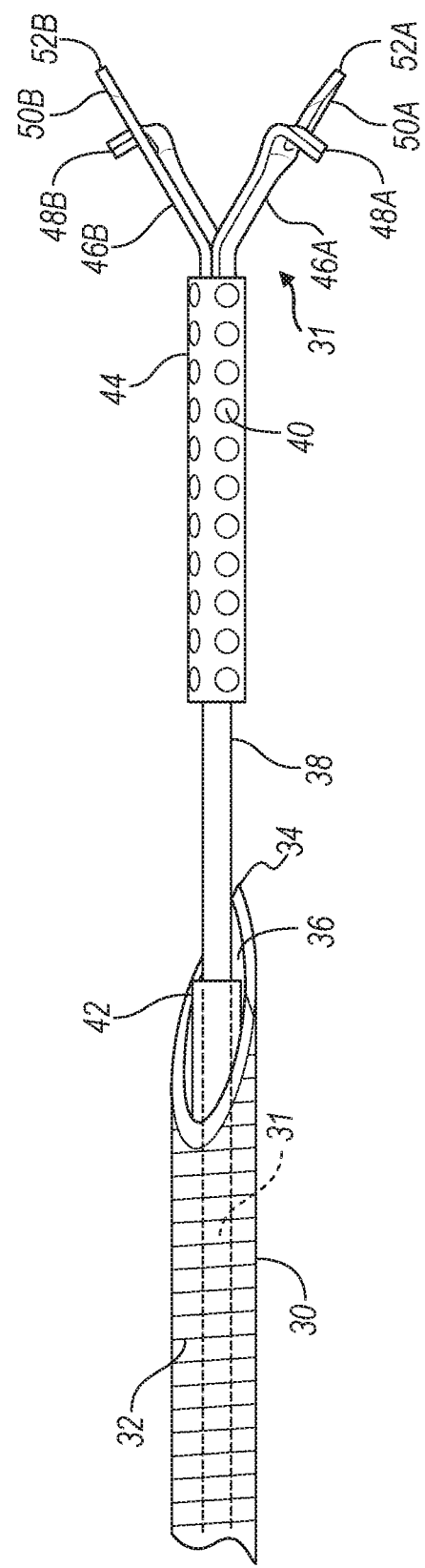
FIG. 2 is a perspective view of a distal portion of the electrosurgical device shown in FIGS. 1A and 1B.

The following description is merely exemplary in nature and is not intended to limit the present disclosure, application, or uses.

Referring now to the drawings, an electrosurgical device embodying the principles of the present invention is illustrated in FIGS. 1A and 1B designated at 10. The electrosurgical device 10 includes an electrode handle 12 and a needle handle 14 positioned within the electrode handle 12. A set of leads 11 extend from the electrode handle 12 and the needle handle 14 to, for example, a controller, as well as a power supply that is selectively controlled to energize the electrosurgical device 10. The electrode handle 12 is coupled to a sheath clamp 22 with a depth setter 20. The electrosurgical device 10 further includes an adapter 26 that enables the electrosurgical device to be connected to an instrument, such as, for example, a bronchoscope.

Referring further to FIG. 2, a needle 30 is connected to the needle handle 14 and extends through a sheath 28 coupled to the sheath clamp 22. The sheath 28 is coupled to the needle handle 14 with a depth setter 20. After advancing the sheath 28 to a desired location, an operator of the electrosurgical device 10, such as a physician, is able to lock the sheath clamp 22 to the sheath by tightening a sheath screw 24 to set the sheath 28. The electrode handle 12 is movable relative to the depth setter 20 along a set of notches 21. An indicator, such as a set of numbers 23, provides a visual reference to the operator as to the depth of the electrode 31. To lock the position of the needle 30, the operator tightens a needle handle screw 16, and to lock the position of an electrode 31 at a desired depth, the operator tightens an electrode handle screw 18 into a particular notch of the set of notches 21. Operation of the electrosurgical device 10 is described in greater detail below.

The needle 30 has a distal end with a point 34 and an interior surface that devices a lumen 36. The electrode 31 is positioned within the lumen 36. The electrode 31 is moveable relative to the needle 30 such that in a first position the electrode's distal end resides within the lumen 36 and in a second position the electrode's distal end extends beyond the distal end of the needle 30 as illustrated in FIG. 2.

The electrode 31 includes a wire 38 connected to a pair of anchors 46A and 46B with a tube 44 crimped to the wire 38 and the anchors 46A and 46B. An insulator 42 surrounds the wire 38 to electrically isolate the needle 30 from the electrode 31. In various implementations, either or both the needle 30 and the tube 44 include echogenic features for visualization of the needle 30 and the electrode 31. For example, the needle 30 can include echogenic features such as, for example, a plurality of circular slots 32 spaced apart along a portion of the exterior of the needle 30, that the tube 44 can include echogenic features such as, for example, a plurality of dents 40 distributed about the exterior surface of the tube 44. Metals such as stainless steel or a shape memory alloy, such as nitinol, can be used to manufacture the needle 30 or the wire 38. Such materials may be well visualized under X-ray or fluoroscopy. In cases where no ultrasound is provided at the distal end of an endoscope, for example, positioning of the electrodes can be accomplished using X-ray or fluoroscopy alone.

In the arrangement shown in FIG. 2, each anchor 46A, 46B includes a curved member 48A and 48B, respectively, which latches the anchors 46A and 46B onto a predetermined portion of tissue of a patient. The anchors 46A and 46B further include piercing members 50A and 50B with tips 52A and 52B that pierce into the predetermined portion of tissue.

Figure 3:
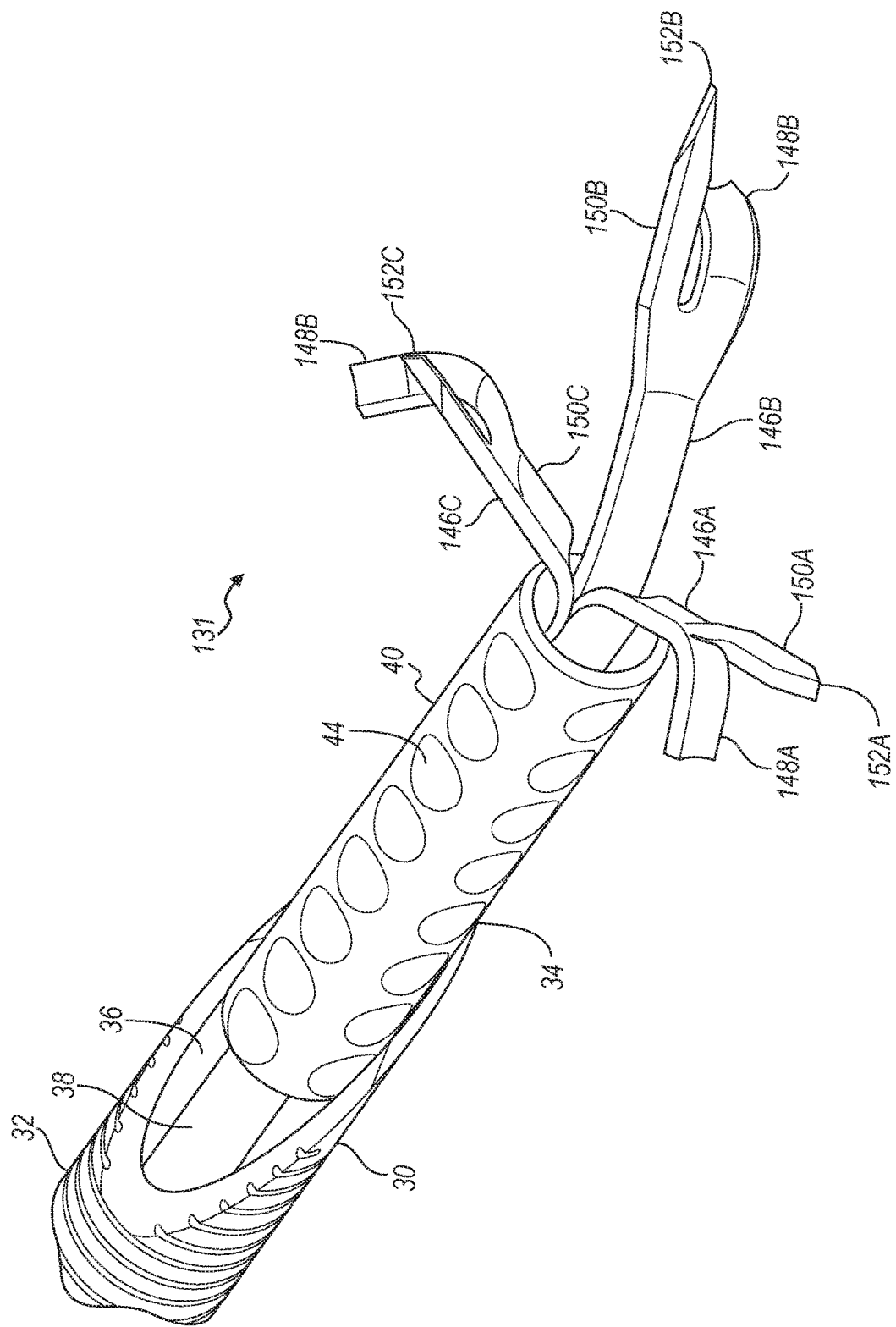
FIG. 3 is a perspective view of another distal portion of the electrosurgical device shown in FIGS. 1A and 1B.

Other arrangements for an electrode are contemplated as well. For example, as shown in FIG. 3, an electrode 131 includes three anchors 146A, 146B, and 146C. Each anchor 146A, 146B, 146C includes a curved member 148A, 148B, and 148C, respectively, that latches the anchors 146A, 146B, and 146C onto a predetermined portion of tissue of a patient. The anchors 146A, 146B, and 148C further include piercing members 150A, 150B, and 150C with tips 152A, 152B, and 152C that pierce into the predetermined portion of tissue.

Figure 4:
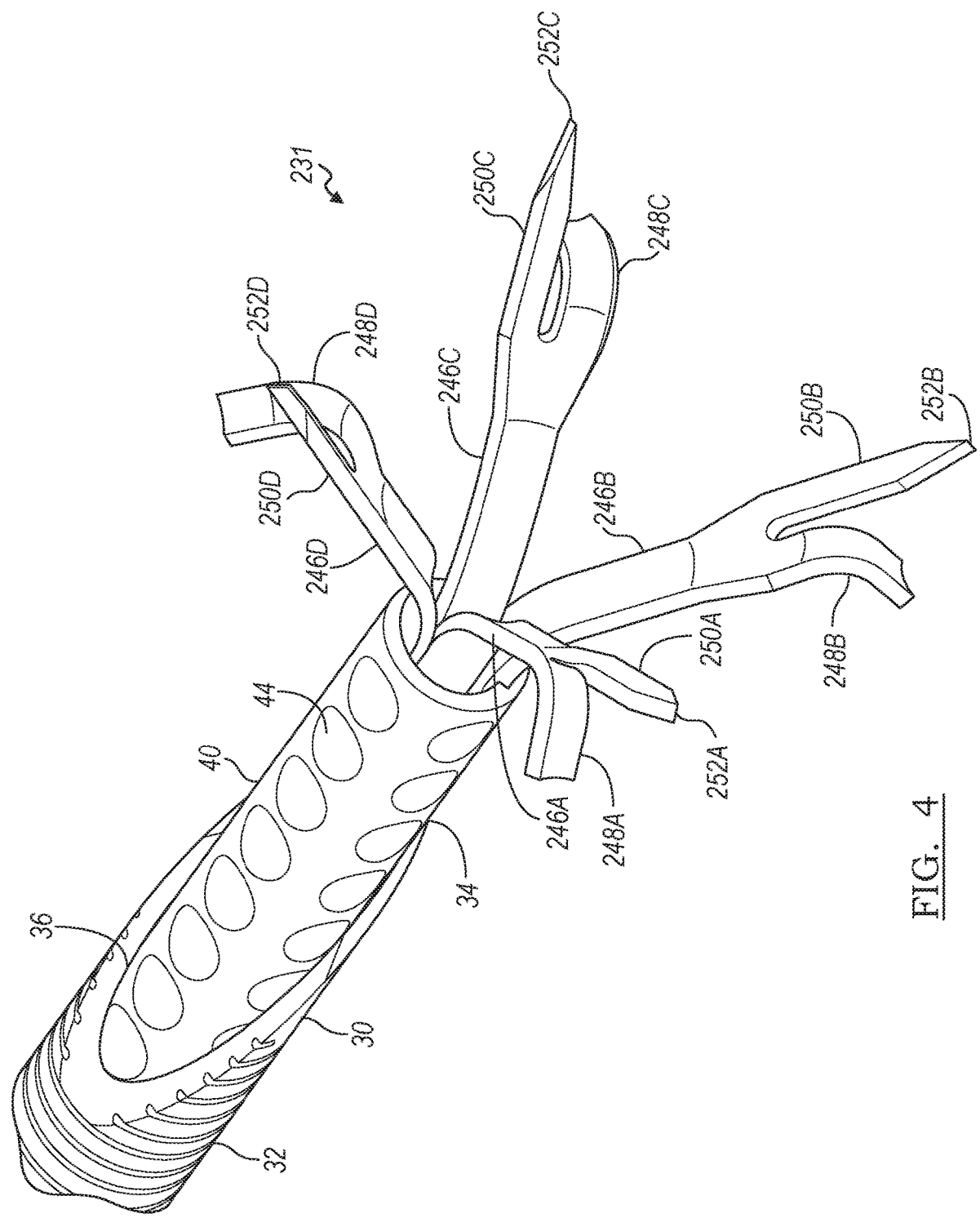
FIG. 4 is a perspective view of yet another distal portion of the electrosurgical device shown in FIGS. 1A and 1B.

In yet another arrangement, as shown in FIG. 4, an electrode 231 includes three anchors 246A, 246B, 246C, and 246D. Each anchor 246A, 246B, 246C, 246D includes a curved member 248A, 248B, 248C, and 248D respectively, that latches the anchors 246A, 246B, 246C, and 246D onto a predetermined portion of tissue of a patient. The anchors 246A, 246B, 248C, and 248D further include piercing members 250A, 250B, 250C, and 250D with tips 252A, 252B, 252C, and 252D that pierce into the predetermined portion of tissue.

Figure 5:
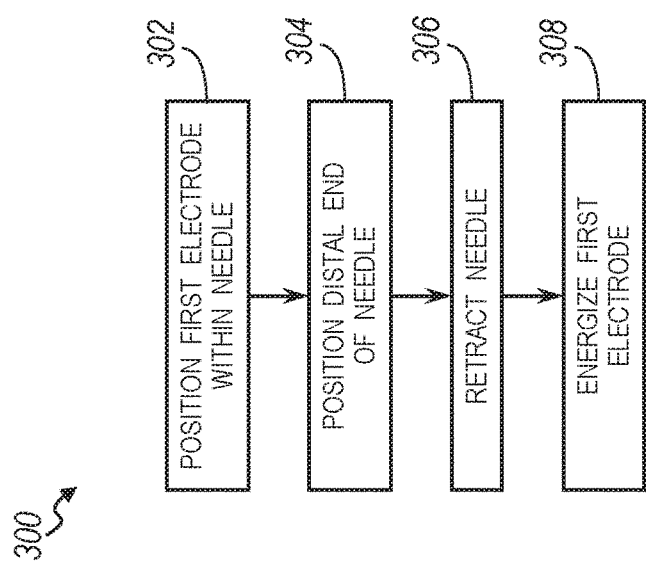
FIG. 5 is a flow diagram of a process for using the electrosurgical device shown in FIGS. 1A and 1B.

In various other arrangements, the electrode can include as few as a single anchor or more than four anchors. With any of the electrode arrangements, the electrode 31, 131, or 231 functions as a first electrode and the needle 30 functions as a second electrode. As such, referring to FIG. 5, there is shown a process 300 with a sequence of steps to operate the electrosurgical device 10.

In a first step 302, the physician positions the first electrode 31,131, or 231 within the needle 30. Subsequently, in a step 304, the physician positions the distal tip 34 of the needle 30 at a predetermined portion of tissue of a patient. The physician, in a step 306, then retracts the needle 30 and, in a step 308, energizes the first electrode 31, 131, or 231 with a desired energy level to ablate the predetermined portion of tissue.

More specifically,

A) to insert the needle 30 and the electrode 31, 131, or 231 into the predetermined portion of tissue, the operator of the electrosurgical device 10 such as a physician:
   1) tightens the needle handle screw 16, which locks the electrode handle 12 to the needle handle 14;
   2) with the needle 30 and the electrode 31,131, or 231 retracted into the sheath 28, inserts the electrosurgical device 10 into a bronchoscope that is already inserted into the patient, and locks the electrosurgical device 10 onto the bronchoscope with bronchoscope adapter 26;

3) advances the sheath 28 and tightens the sheath screw 24 to set the depth of the sheath 28;
4) loosens the electrode handle screw 18 and moves the electrode handle 12 to position the needle 30 into the predetermined portion of tissue;
5) after positioning the needle 30 and the electrode 31 at the desired location, tightens the electrode handle screw 18 to lock the electrode 31 to the depth setter 20 and to prevent movement of the electrode 31, such that all movable components are locked in place;
6) loosens the needle handle screw 16 to allow the needle 30 to slide within the electrode handle 12;
7) slides the needle handle 14 back to expose the electrode 31 and tightens the needle handle screw 16 to lock the needle handle 14 in place;
8) coagulates tissue using an electrical generator coupled to the electrosurgical device 10;
9) pumps saline through a saline manifold into the electrosurgical device 10; and
10) repeats steps 4-9 as necessary to coagulate the predetermined portion of tissue.

B) To remove the electrosurgical device 10 from the patient, the physician:
1) loosens the needle handle screw 16 and slides the needle handle 14 forward to fully capture the electrode 31,131, or 231 within the needle 30;
2) tightens the needle handle screw 16 to lock the needle handle and electrode handle 12 together;
3) loosens the electrode handle screw 16 and moves the electrode handle 12 to retract the needle 30;
4) tightens the electrode handle screw 18 down, when the needle 30 and the electrode 31, 131, or 231 are fully retracted back into the sheath 28;
5) loosens the sheath screw 24, retracts the sheath, and then retightens the sheath screw 24 so that all movable components are locked in place;
6) unlocks the electrosurgical device 10 from the bronchoscope with the bronchoscope adapter; and
7) pulls the electrosurgical device 10 out of the bronchoscope.

Figure 6:
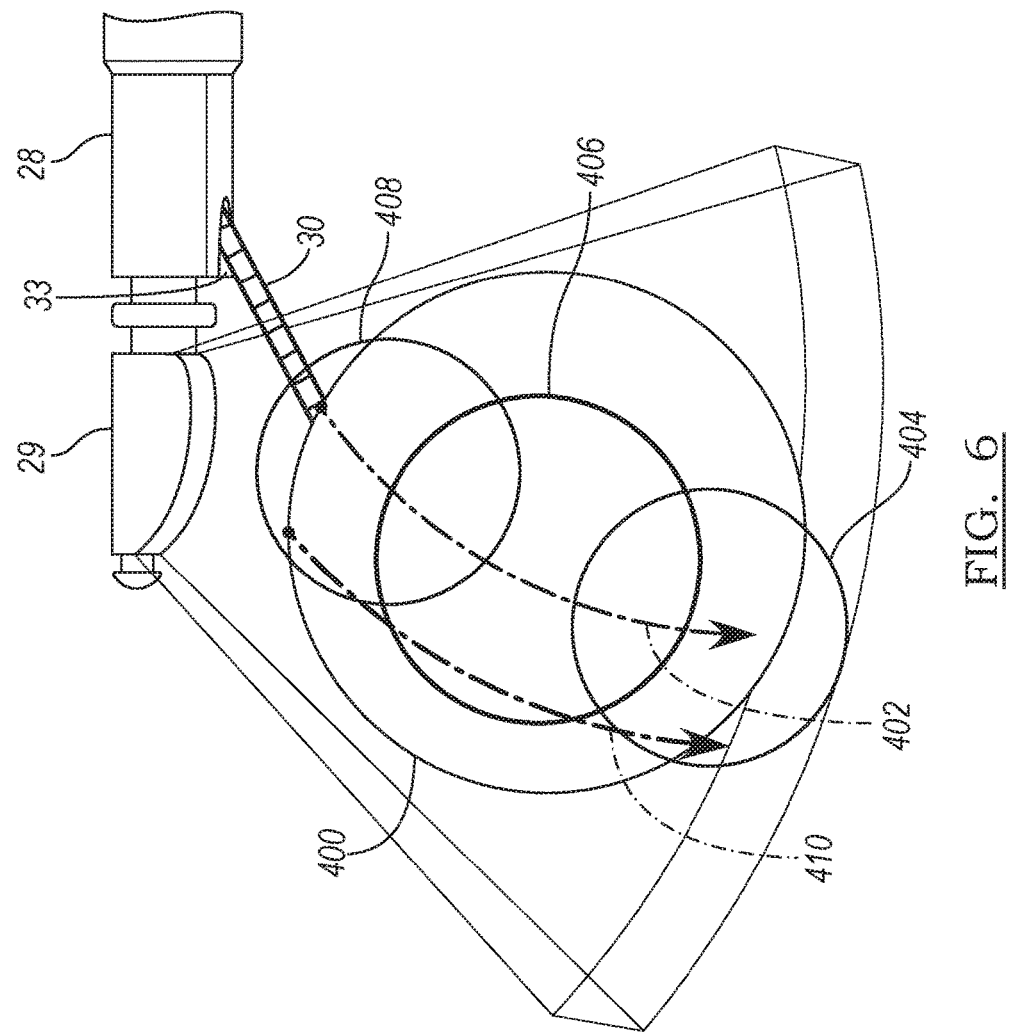
FIG. 6 is a side view showing a process for using the electrosurgical device shown in FIGS. 1A and 1B.

Turning now to FIG. 6, there is shown the needle 30 being employed in an ablation process. The needle 30 exits an opening 33 at a distal end 29 of the sheath 28. The needle 30 is inserted into a target region 400 in the interior region of a patient such that the operator is provided with a consistent method of using the needle 30 in combination with any of the aforementioned electrodes 31, 131, or 231 for coagulating tissue and creating a reproducible coagulation volume in the target region 400.

In addition, FIG. 6 shows an ablation process or pathline technique that takes into account issues associated with over-penetration and potential saline drainage. The pathline technique maximizes the efficiency of coagulation by ensuring that the operator moves the needle 30 and the electrode 31, 131 or 231 as tissue conductivity decreases, effectively creating a larger coagulation volume then attempting to coagulate tissue in a single location.

More specifically, the needle 30 utilizes the needle track created during penetration into the target 400 region to coagulate tissue along a needle path 402, starting at the deepest location 404 initially to seal the needle path. The operator retracts the needle 30 to, for example, a middle location 406 and coagulates tissue in this region if desired, and then retracts the needle 30 to the proximal edge 408 of the target region 400 and coagulates tissue in this region if desired. Hence, the operator is procedurally able to coagulate tissue at locations along the needle path 402 that are closer to the initial penetration location. The pathline technique creates a more consistent and reproducible coagulation volume, while reducing the limitations of high tissue impedance. Once a first portion of the target region has been coagulated, the operator may reinsert the needle 30 and the electrode 31, 131, or 231 along a second path 410 and coagulate in the same manner as the first path 402.

The description of the invention is merely exemplary in nature and variations that do not depart from the gist of the invention are intended to be within the scope of the invention. Such variations are not to be regarded as a departure from the spirit and scope of the invention.

What is claimed is:

1. An electrosurgical device for treating a patient comprising:
   a needle with an interior surface defining a lumen; and
   a first electrode positioned within the lumen of the needle in a first position, the first electrode being movable within the needle between the first position and a plurality of other positions, the first electrode extending beyond a distal end of the needle in the plurality of other positions, the first electrode having one or more anchors with a first distal member and a second distal member, the first distal member being a straight tip that pierces into a predetermined portion of tissue and the second distal member being curved relative to the first distal member, the second distal member latching onto the predetermined portion of tissue to secure the first electrode to the predetermined portion of tissue,
   wherein the first electrode is energized to ablate the predetermined portion of tissue with the first electrode when at each of the plurality of other positions starting with the position being furthest away from the needle.

2. The electrosurgical device of claim 1, wherein the needle serves as a second electrode, the first electrode and the needle arranged to deliver a desired level of energy to the predetermined portion of tissue when the first electrode is in the plurality of other positions to ablate the predetermined portion of tissue.

3. The electrosurgical device of claim 1, further comprising an insulator that electrically isolates the needle from the first electrode.

4. The electrosurgical device of claim 1, wherein the needle has echogenic features on the exterior of the needle.

5. The electrosurgical device of claim 4, wherein the echogenic features are a plurality of circular slots spaced apart along a portion of the exterior of the needle.

6. The electrosurgical device of claim 1, wherein the first electrode is attached to a wire that extends through the lumen of the needle.

7. The electrosurgical device of claim 6, wherein the wire is made of a shape memory alloy.

8. The electrosurgical device of claim 7, wherein the shape memory alloy is nitinol.

9. The electrosurgical device of claim 6, wherein the first electrode is attached to the wire with a tube crimped to the first electrode and the wire.

10. The electrosurgical device of claim 9, wherein the tube incudes echogenic features.

11. The electrosurgical device of claim 10, wherein the echogenic features are a plurality of dents distributed about the exterior of the tube.

12. A method of treating a predetermined portion of tissue in a patient's anatomy comprising:
  positioning a first electrode within a lumen of a needle, the first electrode having one or more anchors with a first distal member and a second distal member, the first distal member being a straight tip and the second distal member being curved relative to the first distal member;
  positioning a distal end of the needle at the predetermined portion of tissue;
  retracting the needle relative to the first electrode so that the first electrode extends beyond the distal end of the needle;
  piercing the straight tip of the first distal member into the predetermined portion of tissue;
  latching the second distal member onto the predetermined portion of tissue to secure the first electrode to the predetermined portion of tissue;
  energizing the first electrode to ablate the predetermined portion of tissue with the first electrode;
  moving the first electrode to a position closer to the needle; and
  energizing the first electrode to ablate the predetermined portion of tissue with the first electrode.

13. The method of claim 12, wherein the needle serves as a second electrode, the first electrode and the needle arranged to deliver a desired level of energy to the predetermined portion of tissue when the first electrode is in position to ablate the predetermined portion of tissue.

14. The method of claim 12, wherein at least one of the one or more anchors includes a tip that pierces into the predetermined portion of tissue and a curved member that latches onto the predetermined portion of tissue to secure the first electrode to the predetermined portion of tissue.

* * * * *